(12) United States Patent
Yamanaka et al.

(10) Patent No.: US 8,871,504 B2
(45) Date of Patent: Oct. 28, 2014

(54) METHOD OF SELECTING SAFE PLURIPOTENT STEM CELLS

(75) Inventors: Shinya Yamanaka, Kyoto (JP); Mari Ohnuki, Kyoto (JP)

(73) Assignee: Kyoto University, Kyoto (JP)

( * ) Notice: Subject to any disclaimer, the term of this patent is extended or adjusted under 35 U.S.C. 154(b) by 193 days.

(21) Appl. No.: 13/393,103

(22) PCT Filed: Sep. 2, 2010

(86) PCT No.: PCT/JP2010/065453
§ 371 (c)(1),
(2), (4) Date: Mar. 23, 2012

(87) PCT Pub. No.: WO2011/027908
PCT Pub. Date: Mar. 10, 2011

(65) Prior Publication Data
US 2012/0171717 A1 Jul. 5, 2012

Related U.S. Application Data

(60) Provisional application No. 61/239,297, filed on Sep. 2, 2009.

(51) Int. Cl.
*C12N 5/00* (2006.01)
*C12N 15/00* (2006.01)

(52) U.S. Cl.
USPC .......................................... 435/325; 435/455

(58) Field of Classification Search
USPC ................................................. 435/325, 455
See application file for complete search history.

(56) References Cited

U.S. PATENT DOCUMENTS

2012/0129172 A1 5/2012 Okano et al.

FOREIGN PATENT DOCUMENTS

WO WO 2010/137348 A1 12/2010

OTHER PUBLICATIONS

Takahashi (Cell, 2006, vol. 126:663-676).*
Takahashi (Cell, 2007, vol. 131: 861-872).*
Maherali (Cell Stem Cell, Jul. 2007, vol. 1, p. 55-70).*
Okita (Nature, Jul. 19, 2007, vol. 448, p. 313-317).*
Wernig (Nature, Jul. 19, 2007, vol. 448, p. 318-324).*
Yu (Science, 2007, vol. 318, p. 1917-1920).*
Blelloch (Cell Stem Cell, Sep. 13, 2007, vol. 1, p. 245-247).*
Nakagawa (Nat Biotechnol, Jan. 2008, vol. 26: 101-106; published online Nov. 11, 2007).*
Jaenisch (Cell, Feb. 22, 2008, vol. 132, p. 567-582).*
Duinsbergen (Experimental Cell Res. Jul. 9, 2008, vol. 314, p. 3255-3263).*
Kim (Nature, Jul. 31, 2008, vol. 454, p. 646-651).*
Aoi (Science, Aug. 2008, vol. 321, p. 699-702; published online Feb. 14, 2008).*
Kim (Cell, Feb. 6, 2009, vol. 136, p. 411-419).*
Gonzalez (PNAS, Jun. 2, 2009, vol. 106, No. 22, p. 8918-8922).*
Stadtfeld (Genes & Develop. 2010, vol. 24, p. 2239-2263).*
Patel (Stem Cell Rev. Sep. 2010, vol. 6, No. 3, p. 367-380).*
Eiges et al., *Current Biology*, 11: 514-518 (2001).
Hentze et al., *Trends in Biotechnology*, 25(1): 24-32 (2006).
Kolossov et al., *J. Exp. Med.*, 203(10): 2315-2327 (2006).
Miura et al., *Nature Biotechnology*, 27(8): 743-745 (2009).
Yamanaka, Shinya, *Cell*, 137(1): 13-17 (2009).
Japanese Patent Office; International Search Report in International Patent Application No. PCT/JP2010/065453 (Dec. 7, 2010).
International Bureau of WIPO, International Preliminary Report on Patentability in International Patent Application No. PCT/JP2010/065453 (Mar. 6, 2012).

* cited by examiner

*Primary Examiner* — Michael C. Wilson
(74) *Attorney, Agent, or Firm* — Leydig, Voit & Mayer, Ltd.

(57) ABSTRACT

Provided is a method of selecting highly safe pluripotent stem cells that do not exhibit differentiation resistance, comprising the steps of (1) inducing a pluripotent stem cell to differentiate, (2) culturing the cell under conditions for maintaining undifferentiated state, (3) detecting the generation of an undifferentiated cell by the cultivation, and comparing the finding with a control, and (4) selecting a pluripotent stem cell whose detected value is not more than a control generation value.

12 Claims, 3 Drawing Sheets

A: 1A2

C: 212C6

B: 335D1

D: 256D4

METHOD OF SELECTING SAFE PLURIPOTENT STEM CELLS

This application is based on U.S. provisional patent application No. 61/239,297 filed on Sep. 2, 2009, the contents of which are hereby incorporated by reference.

TECHNICAL FIELD

The present invention relates to a method of selecting a highly safe pluripotent stem cell, more specifically to a method of selecting a pluripotent stem cell that does not exhibit differentiation resistance, comprising the steps of (1) inducing a pluripotent stem cell to differentiate, (2) culturing the cell under conditions for maintaining the undifferentiated state, (3) detecting the generation of an undifferentiated cell by the cultivation, and comparing the finding with a control, and (4) selecting a pluripotent stem cell whose detected value is not more than a control generation value.

BACKGROUND ART

In recent years, mouse and human induced pluripotent stem cells (iPS cells) have been established one after another. Yamanaka et al. induced iPS cells by introducing the Oct3/4, Sox2, Klf4 and c-Myc genes into mouse fibroblasts, and forcing the cells to express the genes [WO 2007/069666 A1; Takahashi, K. and Yamanaka, S., Cell, 126: 663-676 (2006)]. Thereafter, it was revealed that iPS cells could also be produced with the 3 factors other than the c-Myc gene [Nakagawa, M. et al., Nat. Biotechnol., 26: 101-106 (2008)]. Furthermore, Yamanaka et al. succeeded in establishing iPS cells by introducing the same 4 genes as those used in the mouse into human skin fibroblasts [WO 2007/069666 A1; Takahashi, K. et al., Cell, 131: 861-872 (2007)]. On the other hand, a group of Thomson et al. produced human iPS cells using Nanog and Lin28 in place of Klf4 and c-Myc [WO 2008/118820 A2; Yu, J. et al., Science, 318: 1917-1920 (2007)]. The iPS cells thus obtained can be differentiated into cells of various tissues after being generated using a cell derived from a patient to be treated, and are therefore expected as a graft source free of rejective reactions in the field of regenerative medicine.

However, tumorigenesis has been reported in relation to transplantation of neurons induced to differentiate from an iPS cell to the mouse brain [Miura K. et al., Nat. Biotechnol., 27: 743-745 (2009)], although tumors are not formed in all neurons derived from the iPS cell. It has been suggested that the starting cell for the establishment of the iPS cell may have a major influence, but no method of generating an iPS cell that ensures the absence of tumorigenesis has been established.

Therefore, there is a demand for a method of selecting an iPS cell that is unlikely to form a tumor when transplanted, out of established iPS cells. As stated above, however, testing by transplantation is too painstaking and takes a long time for judgment.

CITED REFERENCES

1. WO 2007/069666 A1
2. Takahashi, K. and Yamanaka, S., Cell, 126: 663-676 (2006)
3. Nakagawa, M. et al., Nat. Biotechnol., 26: 101-106 (2008)
4. Takahashi, K. et al., Cell, 131: 861-872 (2007)
5. WO 2008/118820 A2
6. Yu, J. et al., Science, 318: 1917-1920 (2007)
7. Miura K. et al., Nat. Biotechnol., 27: 743-745 (2009)

SUMMARY OF THE INVENTION

There is a need of efficiently selecting safe pluripotent stem cells suitable for clinical applications. Accordingly, it is an object of the present invention to provide a means of selectively eliminating pluripotent stem cells, particularly human pluripotent stem cells, that exhibit differentiation resistance by retaining pluripotency after differentiation induction.

Aiming at solving the problem described above, the present inventors conducted an investigation in which pluripotent stem cells were induced to differentiate under appropriate conditions, subsequently cultured under conditions for maintaining the undifferentiated state, and examined for the generation of undifferentiated cells. It was found that embryonic stem cells (ES cells), which are pluripotent stem cells confirmed not to cause tumorigenesis even after being transplanted to living organisms, are less likely to produce undifferentiated cells again, whereas induced pluripotent stem cells (iPS cells), which have been confirmed to cause tumorigenesis and exhibit differentiation resistance, are more likely to produce undifferentiated cells.

With these results in mind, the present inventors further investigated and found that pluripotent stem cells that do not exhibit differentiation resistance can be selected by conducting differentiation induction of pluripotent stem cells under appropriate conditions, then culturing the cells under conditions for maintaining the undifferentiated state, counting the undifferentiated cells generated, and selecting pluripotent stem cells exhibiting a low count of the undifferentiated one, and have developed the present invention.

Accordingly, the present invention provides:
[1] A method of selecting a pluripotent stem cell that does not exhibit differentiation resistance, comprising the steps of:
(1) inducing a pluripotent stem cell to differentiate,
(2) culturing the cell under conditions for maintaining the undifferentiated state,
(3) detecting the generation of an undifferentiated cell by the cultivation, and comparing the finding with a control, and
(4) selecting a pluripotent stem cell whose detected value is not more than a control generation value.
[2] The method according to [1], wherein the step of differentiation induction comprises treating the pluripotent stem cell with retinoic acid.
[3] The method according to [2], wherein the retinoic acid concentration is not less than 300 nM and not more than 1000 nM.
[4] The method according to [2], wherein the duration of retinoic acid treatment is 4 days.
[5] The method according to [1], wherein the step of cultivation under conditions for maintaining the undifferentiated state comprises cultivation on feeder cells.
[6] The method according to [1], wherein the pluripotent stem cell is an induced pluripotent stem cell.
[7] The method according to [1], wherein the control is an embryonic stem cell.
[8] The method according to [1], wherein the step of detecting the generation of an undifferentiated cell comprises measuring the number of colonies formed.
[9] The method according to [8], wherein the control generation value obtained when differentiation is induced by 300 nM retinoic acid treatment is 300 colonies of undifferentiated cells generated per 200000 cells induced to differentiate.
[10] The method according to [8], wherein the control generation value obtained when differentiation is induced by 300 nM retinoic acid treatment is 250 colonies of undifferentiated cells generated per 200000 cells induced to differentiate.

[11] The method according to [8], wherein the control generation value obtained when differentiation is induced by 300 nM retinoic acid treatment is 216 colonies of undifferentiated cells generated per 200000 cells induced to differentiate.

[12] The method according to claim [8], wherein the control generation value obtained when differentiation is induced by 1000 nM retinoic acid treatment is 50 colonies of undifferentiated cells generated per 200000 cells induced to differentiate.

[13] The method according to claim [8], wherein the control generation value obtained when differentiation is induced by 1000 nM retinoic acid treatment is 20 colonies of undifferentiated cells-generated per 200000 cells induced to differentiate.

[14] The method according to claim [8], wherein the control generation value obtained when differentiation is induced by 1000 nM retinoic acid treatment is 14 colonies of undifferentiated cells generated per 200000 cells induced to differentiate.

[15] The method according to [1], wherein the step of detecting the generation of an undifferentiated cell comprises measuring the ratio of the number of colonies formed from a cell induced to differentiate to the number of colonies formed while in the undifferentiated state.

[16] The method according to [15], wherein the control generation value obtained when differentiation is induced by 300 nM retinoic acid treatment is 1%.

[17] The method according to [15], wherein the control generation value obtained when differentiation is induced by 300 nM retinoic acid treatment is 0.6%.

[18] The method according to [15], wherein the control generation value obtained when differentiation is induced by 300 nM retinoic acid treatment is 0.58%.

According to the present invention, it is possible to select a pluripotent stem cell suitable for differentiation induction of cells and tissues for transplantation that does not exhibit differentiation resistance. The present invention is therefore highly useful in applying pluripotent stem cells, particularly iPS cells, to regenerative medicine.

DESCRIPTION OF EMBODIMENTS

Figure 1:
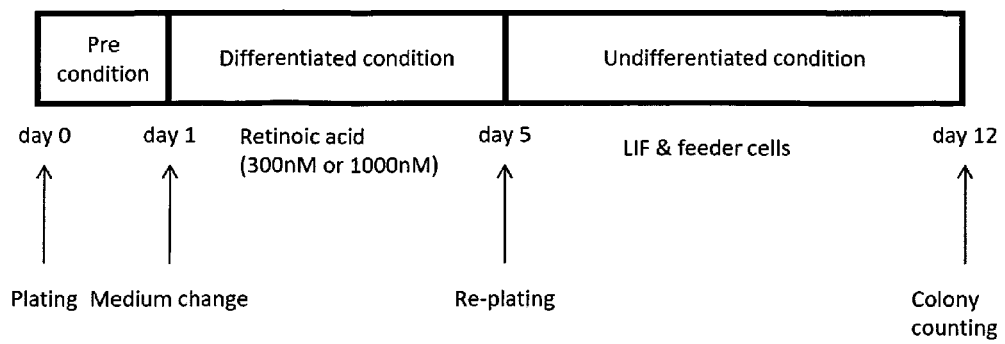
FIG. 1 shows an experimental protocol.

The present invention provides a method of sorting pluripotent stem cells that exhibit differentiation resistance and pluripotent stem cells that do not, by returning pluripotent stem cells to conditions for maintaining the undifferentiated state after differentiation induction, and examining whether cells in the undifferentiated state remain. Here, "a pluripotent stem cell that exhibits differentiation resistance" means a pluripotent stem cell wherein a distinct property of stem cells, "the potential for self-replication", is abnormally predominant over "the potential for differentiation", another distinct property of stem cells, that is, a pluripotent stem cell at an increased risk of forming a tumor after being transplanted after differentiation induction because of the retention of pluripotency due to self-replication in some cells, despite that the majority of cells have differentiated into desired cells when induced to differentiate into the desired cells. Specifically, a pluripotent stem cell that exhibits differentiation resistance in the present invention is a pluripotent stem cell likely to form a tumor to an extent exceeding a usually observed level in normal embryonic stem cells (ES cells) when induced to differentiate into desired cells and transplanted to a host.

I. Pluripotent Stem Cells

In the present invention, "a pluripotent stem cell" refers to a cell that maintains undifferentiated state and pluripotency, represented by embryonic stem cells (ES cells) and induced pluripotent stem cells (iPS cells). This ES cell may be an ES cell resulting from nuclear reprogramming of a somatic cell. Besides ES cells, examples include embryonic germ cells (EG cells) derived from primordial germ cells, multipotent germline stem cells (mGS cells) isolated from the testis, multipotent adult progenitor cells (MAPCs) isolated from the bone marrow and the like. These pluripotent stem cells may be derived from any mammal (e.g., humans, mice, monkeys, pigs, rats and the like).

The procedures for producing iPS cells in the present invention are described below.

II. Procedures for Producing iPS Cells (A) Source of Somatic Cells

Any cells other than germ cells of mammalian origin (e.g., humans, mice, monkeys, pigs, rats etc.) can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), contractile cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells thereof (tissue progenitor cells) and the like. There is no limitation on the degree of cell differentiation, the age of the animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as neural stem cells, hematopoietic stem cells, mesenchymal stem cells, and dental pulp stem cells.

The choice of mammal individual as a source of somatic cells is not particularly limited; however, when the iPS cells obtained are to be used for the regenerative medicine in humans, it is preferable, from the viewpoint of prevention of graft rejection to collect the somatic cells from the patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR) are identical and the like (hereinafter the same meaning shall apply). When the iPS cells obtained are not to be administered (transplanted) to a human, but used as, for example, a source of cells for screening for evaluating a patient's drug susceptibility or adverse reactions, it is likewise desirable to collect the somatic cells from the patient or another person with the same genetic polymorphism correlating with the drug susceptibility or adverse reactions.

Before being subjected to the step of nuclear reprogramming, somatic cells separated from a mammal can be pre-cultured using a medium known per se suitable for the cultivation thereof, depending on the kind of the cells. Examples of such media include, but are not limited to, a minimal essential medium (MEM) containing about 5 to 20% fetal calf serum, Dulbecco's modified Eagle medium (DMEM), RPMI1640 medium, 199 medium, F12 medium and the like. When using, for example, a transfection reagent such as a cationic liposome in contacting the cell with a nuclear reprogramming substance and a functional inhibitor of p53 (and another iPS cell establishment efficiency improver as required), it is sometimes preferable that the medium be previously replaced with a serum-free medium to prevent a reduction in the transfer efficiency.

(B) Nuclear Reprogramming Substances

In the present invention, "a nuclear reprogramming substance" can be a proteinous factor (proteinous factors) capable of inducing an iPS cell from a somatic cell or a nucleic acid that encodes the same (including forms incorporated in a vector). The nuclear reprogramming substance used in the present invention may be a gene described in WO 2007/069666. More specifically, examples include Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Nanog, Esrrb or Esrrg. These reprogramming substances may be used in combination in establishing an iPS cell, the combination being a combination containing at least 1, 2 or 3 of the above-described reprogramming substances, preferably a combination containing 4 of them. Specifically, the nuclear reprogramming substances used in the present invention are exemplified by the following combinations (here, only the names for proteinous factors are shown).

(1) Oct3/4, Klf4, Sox2, c-Myc (here, Sox2 is replaceable with Sox1, Sox3, Sox15, Sox17 or Sox18; Klf4 is replaceable with Klf1, Klf2 or Klf5; c-Myc is replaceable with L-Myc or N-Myc)
(2) Oct3/4, Klf4, Sox2, c-Myc, TERT, SV40 Large T antigen (hereinafter, SV40LT)
(3) Oct3/4, Klf4, Sox2, c-Myc, TERT, HPV16 E6
(4) Oct3/4, Klf4, Sox2, c-Myc, TERT, HPV16 E7
(5) Oct3/4, Klf4, Sox2, c-Myc, TERT, HPV6 E6, HPV16 E7
(6) Oct3/4, Klf4, Sox2, c-Myc, TERT, Bmi1
(7) Oct3/4, Klf4, Sox2, c-Myc, Lin28
(8) Oct3/4, Klf4, Sox2, c-Myc, Lin28, SV40LT
(9) Oct3/4, Klf4, Sox2, c-Myc, Lin28, TERT, SV40LT
(10) Oct3/4, Klf4, Sox2, c-Myc, SV40LT
(11) Oct3/4, Esrrb, Sox2, c-Myc (Esrrb is replaceable with Esrrg)
(12) Oct3/4, Klf4, Sox2
(13) Oct3/4, Klf4, Sox2, TERT, SV40LT
(14) Oct3/4, Klf4, Sox2, TERT, HPV16 E6
(15) Oct3/4, Klf4, Sox2, TERT, HPV16 E7
(16) Oct3/4, Klf4, Sox2, TERT, HPV6 E6, HPV16 E7
(17) Oct3/4, Klf4, Sox2, TERT, Bmi1
(18) Oct3/4, Klf4, Sox2, Lin28
(19) Oct3/4, Klf4, Sox2, Lin28, SV40LT
(20) Oct3/4, Klf4, Sox2, Lin28, TERT, SV40LT
(21) Oct3/4, Klf4, Sox2, SV40LT
(22) Oct3/4, Esrrb, Sox2 (Esrrb is replaceable with Esrrg)

In the combinations above, Lin28b can be used in place of Lin28.

Any combination that does not fall in (1) to (22) above but comprises all the constituents of any one of (1) to (22) above and further comprises an optionally chosen other substance can also be included in the scope of "nuclear reprogramming substances" in the present invention. Provided that the somatic cell to undergo nuclear reprogramming is endogenously expressing one or more of the constituents of any one of (1) to (22) above at a level sufficient to cause nuclear reprogramming, a combination of only the remaining constituents excluding the one or more constituents can also be included in the scope of "nuclear reprogramming substances" in the present invention.

Of these combinations, 4 factors consisting of Oct3/4, Sox2, Klf4 and c-Myc, and 3 factors consisting of Oct3/4, Sox2 and Klf4 are examples of preferred nuclear reprogramming substances. Also preferred are 6 or 5 factors consisting of the above 4 or 3 factors and additional SV40 Large T antigen.

Information on the mouse and human cDNA sequences of the aforementioned nuclear reprogramming substances is available with reference to the NCBI accession numbers mentioned in WO 2007/069666 (also, mouse and human cDNA sequence information on L-Myc, Lin28, Lin28b, Esrrb and Esrrg can be acquired by referring to the following NCBI accession numbers); those skilled in the art are easily able to isolate these cDNAs.

| Name of gene | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |

A proteinous factor for use as a nuclear reprogramming substance can be prepared by inserting the cDNA obtained into an appropriate expression vector, introducing the vector into a host cell, and recovering the recombinant proteinous factor from the cultured cell or its conditioned medium. Meanwhile, when the nuclear reprogramming substance used is a nucleic acid that encodes a proteinous factor, the cDNA obtained is inserted into a viral vector, plasmid vector, episomal vector etc. to construct an expression vector, and the vector is subjected to the step of nuclear reprogramming.

(c) Method of Transferring Nuclear Reprogramming Substance to Somatic Cell

Transfer of a nuclear reprogramming substance to a somatic cell can be achieved using a method known per se for protein transfer into a cell, provided that the substance is a proteinous factor. Such methods include, for example, the method using a protein transfer reagent, the method using a protein transfer domain (PTD)- or cell penetrating peptide (CPP)-fusion protein, the microinjection method and the like. Protein transfer reagents are commercially available, including those based on a cationic lipid, such as BioPOTER Protein Delivery Reagent (Gene Therapy Systems), Pro-Ject™ Protein Transfection Reagent (PIERCE) and ProVectin (IMGENEX); those based on a lipid, such as Profect-1 (Targeting Systems); those based on a membrane-permeable peptide, such as Penetrain Peptide (Q biogene) and Chariot Kit (Active Motif), GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. Nuclear reprogramming substance(s) is (are) diluted in an appropriate solvent (e.g., a buffer solution such as PBS or HEPES), a transfer reagent is added, the mixture is incubated at room temperature for about 5 to 15 minutes to form a complex, this complex is added to cells after exchanging the medium with a serum-free medium, and the cells are incubated at 37° C. for one to several hours. Thereafter, the medium is removed and replaced with a serum-containing medium.

Developed PTDs include those using transcellular domains of proteins such as drosophila-derived AntP, HIV-derived TAT (Frankel, A. et al, *Cell* 55, 1189-93 (1988) or Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl. Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. Biochem. *Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell*, 4, 381-384 (2009)) and 9R (*Cell Stem Cell*, 4, 472-476 (2009)).

A fused protein expression vector incorporating cDNA of a nuclear reprogramming substance and PTD or CPP sequence is prepared, and recombination expression is performed using the vector. The fused protein is recovered and used for transfer. Transfer can be performed in the same manner as above except that a protein transfer reagent is not added.

Microinjection, a method of placing a protein solution in a glass needle having a tip diameter of about 1 μm, and injecting the solution into a cell, ensures the transfer of the protein into the cell.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 to 48 hours, preferably 12 to 24 hours.

However, taking into account the efficiency of establishment of iPS cells, nuclear reprogramming substance may be used preferably in the form of a nucleic acid that encodes a proteinous factor, rather than the factor as it is. The nucleic acid may be a DNA or an RNA, or a DNA/RNA chimera, and may be double-stranded or single-stranded. Preferably, the nucleic acid is a double-stranded DNA, particularly a cDNA.

A cDNA of a nuclear reprogramming substance is inserted into an appropriate expression vector comprising a promoter capable of functioning in a host somatic cell. Useful expression vectors include, for example, viral vectors such as retrovirus, lentivirus, adenovirus, adeno-associated virus, herpesvirus and Sendai virus, plasmids for the expression in animal cells (e.g., pA1-11, pXT1, pRc/CMV, pRc/RSV, pcDNAI/Neo) and the like.

A vector for this purpose can be chosen as appropriate according to the intended use of the iPS cell to be obtained. Useful vectors include adenovirus vector, plasmid vector, adeno-associated virus vector, retrovirus vector, lentivirus vector, Sendai virus vector, episomal vector and the like.

Examples of promoters used in expression vectors include the EF1α promoter, the CAG promoter, the SRα promoter, the SV40 promoter, the LTR promoter, the CMV (cytomegalovirus) promoter, the RSV (Rous sarcoma virus) promoter, the MoMuLV (Moloney mouse leukemia virus) LTR, the HSV-TK (herpes simplex virus thymidine kinase) promoter and the like, with preference given to the EFla promoter, the CAG promoter, the MoMuLV LTR, the CMV promoter, the SRα promoter and the like.

The expression vector may contain as desired, in addition to a promoter, an enhancer, a polyadenylation signal, a selectable marker gene, a SV40 replication origin and the like. Examples of selectable marker genes include the dihydrofolate reductase gene, the neomycin resistant gene, the puromycin resistant gene and the like.

The nucleic acids which are nuclear reprogramming substances (reprogramming genes) may be separately integrated into different expression vectors, and 2 or more, preferably 2 to 3, different genes may be integrated into a single expression vector. Preference is given to the former case with the use of a retrovirus or lentivirus vector, which offer high transfection efficiency, and to the latter case with the use of a plasmid, adenovirus, or episomal vector and the like. Furthermore, an expression vector incorporating two or more different genes and another expression vector incorporating one gene alone can be used in combination.

In the context above, when a plurality of reprogramming genes [e.g., 2 or more, preferably 2 or 3 different genes, selected from among Oct3/4, Sox2, Klf4 and c-Myc] are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (PLoS ONE 3, e2532, 2008, Stem Cells 25, 1707, 2007), the IRES sequence (U.S. Pat. No. 4,937,190) and the like, with preference given to the 2A sequence.

An expression vector harboring a reprogramming gene can be introduced into a cell by a technique known per se according to the choice of the vector. In the case of a viral vector, for example, a plasmid containing the nucleic acid is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector are disclosed in WO2007/69666, *Cell*, 126, 663-676 (2006) and *Cell*, 131, 861-872 (2007). Specific means using a lentivirus vector is disclosed in *Science*, 318, 1917-1920 (2007).

When iPS cells are utilized as cell sources for regenerative medicine, an expression (reactivation) of a reprogramming gene potentially increases the risk of carcinogenesis in tissues regenerated from differentiated cells derived from iPS cells; therefore, a reprogramming gene is preferably expressed transiently, without being integrated into the chromosome of the cells. From this viewpoint, use of an adenoviral vector, whose integration into chromosome is rare, is preferred. Specific means using an adenoviral vector is disclosed in *Science*, 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.*, 282, 27383-27391 (2007) and JP-3602058 B can be used.

When a retroviral vector or a lentiviral vector is used, even if silencing of the transgene has occurred, it possibly becomes reactivated; therefore, for example, a method can be used preferably wherein a nucleic acid encoding a nuclear reprogramming substance is cut out using the Cre-loxP system, when becoming unnecessary. That is, with loxP sequences arranged on both ends of the nucleic acid in advance, after iPS cells are induced, the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivating (SIN) LTR prepared by deleting the sequence, or substituting the sequence with a polyadenylation sequence such as of SV40. Specific means using the Cre-loxP system and SIN LTR is disclosed in Chang et al., *Stem Cells,* 27: 1042-1049 (2009).

Meanwhile, being a non-viral vector, a plasmid vector can be transferred into a cell using the lipofection method, liposome method, electroporation method, calcium phosphate co-precipitation method, DEAE dextran method, microinjection method, gene gun method and the like. Specific means using a plasmid as a vector are described in, for example, *Science,* 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre-loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature,* 458: 771-775 (2009), Woltjen et al., *Nature,* 458: 766-770 (2009).

Another preferable non-integration type vector is an episomal vector, which is autonomously replicable outside the chromosome. Specific means with the use of an episomal vector is described by Yu et al. in *Science,* 324, 797-801 (2009). In a particularly preferred embodiment of the present invention, by constructing an expression vector by inserting a reprogramming gene into an episomal vector having loxP sequences placed in the same orientation on the 5' and 3' sides of a vector constituent essential for the replication of the episomal vector, and transferring the expression vector to a somatic cell, the vector occurring as an episome is eliminated from the iPS cell at an early stage, without integration, even transient one, of the extraneous nucleic acid factors (including reprogramming genes) that constitute the vector, into the genome of the cell.

Examples of the episomal vector to be used in the present invention include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40.

The episomal expression vector comprises a promoter that controls the transcription of reprogramming genes. The promoter used may be as described above. The episomal expression vector may further contain as desired an enhancer, a polyadenylation signal, a selection marker gene and the like, as described above. Examples of the selection marker gene include the dihydrofolate reductase gene, the neomycin resistance gene and the like.

The episomal vector allows the vector to be introduced into the cell using, for example, the lipofection method, liposome method, electroporation method, calcium phosphate co-precipitation method, DEAE dextran method, microinjection method, gene gun method and the like. Specifically, for example, methods described in *Science,* 324: 797-801 (2009) and elsewhere can be used.

Whether or not the vector component necessary for the replication of the reprogramming gene has been removed from the iPS cell can be confirmed by performing a Southern blot analysis or PCR analysis using a nucleic acid comprising a nucleotide sequence in the vector component as a probe or primer, with the episome fraction isolated from the iPS cell as a template, and determining the presence or absence of a band or the length of the band detected. The episome fraction can be prepared by a method well known in the art; for example, methods described in *Science,* 324: 797-801 (2009) and elsewhere can be used.

(D) Functional Inhibitors of p53

In the present invention, it is more preferable that in addition to the above-described nuclear reprogramming substances, a functional inhibitor of p53 be brought into contact with the starting cell. As mentioned herein, "a functional inhibitor of p53" may be any substance capable of inhibiting either (a) the function of the p53 protein or (b) the expression of the p53 gene. That is, not only substances that act directly on the p53 protein to inhibit the function thereof and substances that act directly on the p53 gene to inhibit the expression thereof, but also substances that act on a factor involved in p53 signal transfection to result in inhibition of the function of the p53 protein or the expression of the p53 gene, are also included in the scope of "a functional inhibitor of p53" as mentioned herein. Preferably, the functional inhibitor of p53 is a substance that inhibits the expression of the p53 gene, more preferably an expression vector that encodes an siRNA or shRNA against p53.

Examples of substances that inhibit the function of the p53 protein include, but are not limited to, a chemical inhibitor of p53, a dominant negative mutant of p53 or a nucleic acid that encodes the same, an anti-p53 antagonist antibody or a nucleic acid that encodes the same, a decoy nucleic acid comprising a consensus sequence of a p53-responsive element, a substance that inhibits the p53 pathway, and the like. Preferably, a chemical inhibitor of p53, a dominant negative mutant of p53 or a nucleic acid that encodes the same, and a p53 pathway inhibitor can be mentioned.

(D1) Chemical Inhibitors of p53

Examples of chemical inhibitors of p53 include, but are not limited to, p53 inhibitors typified by pifithrin (PFT)-α and -β, which are disclosed in WO 00/44364, PFT-μ disclosed in Storm et al. (*Nat. Chem. Biol.* 2, 474 (2006)), analogue thereof and salts thereof (for example, acid addition salts such as hydrochlorides and hydrobromides, and the like) and the like. Of these, PFT-α and analogues thereof [2-(2-Imino-4,5,6,7-tetrahydrobenzothiazol-3-yl)-1-p-tolylethanone, HBr (product name: Pifithrin-α) and 1-(4-Nitrophenyl)-2-(4,5,6,7-tetrahydro-2-imino-3(2H)-benzothiazolyl)ethanone, HBr (product name: Pifithrin-α, p-Nitro)], PFT-β and analogues thereof [2-(4-Methylphenyl)imidazo[2,1-b]-5,6,7,8-tetrahydrobenzothiazole, HBr (product name: Pifithrin-α, Cyclic) and 2-(4-Nitrophenyl)imidazo[2,1-b]-5,6,7,8-tetrahydrobenzothiazole (product name: Pifithrin-α, p-Nitro, Cyclic)], and PFT-μ [Phenylacetylenylsulfonamide (product name: Pifithrin-μ)] are commercially available from Merck.

Contact of a chemical inhibitor of p53 with a somatic cell can be achieved by dissolving the inhibitor at an appropriate concentration in an aqueous or nonaqueous solvent, adding the inhibitor solution to a medium suitable for cultivation of somatic cells isolated from a human or mouse [e.g., minimal essential medium (MEM) comprising about 5 to 20% fetal bovine serum, Dulbecco's modified Eagle medium (DMEM), RPMI1640 medium, 199 medium, F12 medium, and the like] so that the inhibitor concentration will be sufficient to inhibit the function of p53 without causing cytotoxicity, and culturing the cells for a given period. The concentration of the inhibitor varies depending on the choice of the inhibitor used, and is chosen as appropriate over the range of about 0.1 nM to about 100 nM. Duration of contact is not particularly limited, as far as it is sufficient to cause nuclear reprogramming of the cells; usually, the inhibitor may be allowed to be co-present in the medium until a positive colony emerges.

The p53 gene is known as a tumor suppressor gene; permanent inhibition of p53 function potentially increases the risk of carcinogenesis. Chemical inhibitors of p53 are useful, not only because of the advantage of permitting introduction into cells simply by the addition to the medium, but also because of the advantage of permitting termination of the inhibition of p53 function, easily and quickly, by removing the medium containing the inhibitor after induction of iPS cells.

(D2) Dominant Negative Mutants of p53

The choice of dominant negative mutant of p53 is not particularly limited, as far as the mutant is capable of competitively acting against the wild-type p53 protein endogenously expressed in somatic cells to inhibit the function thereof; for example, p53P275S, resulting from point mutation of the proline at the position 275 (in the case of humans, position 278) located in the DNA-binding region of mouse p53 to serine (de Vries, A., *Proc. Natl. Acad. Sci. USA*, 99, 2948-2953 (2002)); p53DD, resulting from deletion of the amino acids at the positions 14-301 of mouse p53 (in human p53, corresponds to the positions 11-304) (Bowman, T., *Genes Develop.*, 10, 826-835 (1996)), and the like can be mentioned. Other known mutants include, for example, p53S58A, resulting from point mutation of the serine at the position 58 of mouse p53 (in the case of humans, position 61) to alanine; p53C135Y, resulting from point mutation of the cysteine at the position 135 of human p53 (in the case of mice, position 132) to tyrosine; p53A135V, resulting from point mutation of the alanine at the position 135 of mouse p53 (in the case of humans, position 138) to valine; p53R172H, resulting from point mutation of the arginine at the position 172 (in the case of humans, position 175) to histidine; p53R270H, resulting from point mutation of the arginine at the position 270 (in the case of humans, position 273) to histidine; p53D278N, resulting from point mutation of the aspartic acid at the position 278 of mouse p53 (in the case of humans, position 281) to asparagine, and the like; these can be used in the same way.

A dominant negative mutant of p53 can be obtained by for example, the technique described below. First, an appropriate oligonucleotide is synthesized as a probe or primer on the basis of the mouse or human p53 cDNA sequence information, and a mouse or human p53 cDNA is cloned from a mRNA, cDNA or cDNA library derived from a mouse or human cell or tissue, using the hybridization method or the (RT-)PCR method, and is subcloned into an appropriate plasmid. In a form wherein a codon of the site into which a mutation is to be introduced is replaced with a codon that encodes another desired amino acid, a primer comprising the site is synthesized, and inverse PCR is performed using this primer with the plasmid incorporating the p53 cDNA as a template, whereby a nucleic acid that encodes the desired dominant negative mutant is acquired. In the case of a deletion mutant like p53DD, a primer may be designed outside the site to be deleted, and inverse PCR may be performed as described above. By introducing the thus-obtained nucleic acid that encodes the dominant negative mutant into a host cell, and recovering a recombinant protein from the cultured cell or its conditioned medium, the desired dominant negative mutant can be acquired.

Contact of a dominant negative mutant with a somatic cell can be achieved in the same manner as with the above-described proteinous nuclear reprogramming substances. As described above, permanent inhibition of p53 function potentially increases the risk of carcinogenesis. However, because a dominant negative mutant of p53 undergoes degradation by protease and disappears gradually in the transfected cell, and correspondingly the function of p53 endogenously expressed in the cell is restored, use of the mutant protein can be suitable in cases where high safety is required as in the utilization of iPS cells for therapeutic purposes.

(D3) Nucleic Acids that Encode Dominant Negative Mutants of p53

In another preferred mode of embodiment of the present invention, the functional inhibitor of p53 is a nucleic acid that encodes a dominant negative mutant of p53. The nucleic acid may be a DNA or an RNA, or a DNA/RNA chimera, and is preferably a DNA. The nucleic acid may be double-stranded or single-stranded. A cDNA that encodes a dominant negative mutant of p53 can be cloned by the technique described above with respect to preparation of the mutant protein.

The cDNA thus isolated, like the aforementioned nucleic acids which are nuclear reprogramming substances (reprogramming genes), can be inserted into an appropriate expression vector and transferred to a somatic cell.

(D4) p53 Pathway Inhibitors

Here, the term p53 pathway is used with a meaning including all upstream signal cascades that can activate p53 and all downstream signal cascades mediated by activated p53. Therefore, p53 pathway inhibitors include all substances that inhibit any one of the aforementioned signal transduction pathways, but in a preferred mode of embodiment, the p53 pathway inhibitor is a substance that inhibits the expression or function (Myc inhibitory activity) of p21, whose transcription is activated by p53; for example, siRNA, shRNA, antisense nucleic acids, ribozymes against p21 and the like can be mentioned. These nucleic acids that inhibit the expression of p21 can be designed and synthesized in the same manner as the method for siRNA, shRNA, antisense nucleic acids, and ribozymes against p53 described below, and can be introduced into a somatic cell. The nucleic acids may be provided in the form of a vector that expresses them, the vector can be constructed in the same manner as the method for a vector that expresses an siRNA, shRNA, antisense nucleic acid, or ribozyme against p53 described below, and introduced into a somatic cell.

In another preferred mode of embodiment, the p53 pathway inhibitor is a substance that inhibits the ARF-MDM2-p53 pathway; for example, as ARF-MDM2-p53 pathway inhibitors, MDM2, which binds directly to p53 to promote the nuclear export or ubiquitination thereof or a nucleic acid that encodes the same, a substance that inhibits the expression or function of p19$^{ARF}$ or ATM (ataxia-telangiectasia mutated), which inhibits the action of MDM2 on p53 (for example, siRNAs and shRNAs against these factors) and the like can be mentioned.

(D5) Other Substances

As examples of other substances that inhibit the function of the p53 protein, anti-p53 antagonist antibody or a nucleic acid that encodes the same can be mentioned. The anti-p53 antagonist antibody may be a polyclonal antibody or a monoclonal antibody. The isotype of the antibody is not particularly limited, and is preferably IgG, IgM or IgA, particularly preferably IgG. The antibody may be, in addition to a complete antibody molecule, for example, a fragment such as Fab, Fab', or F(ab')$_2$, a conjugate molecule prepared by a gene engineering technique, such as scFv, scFv-Fc, minibody, or diabody, or a derivative thereof modified with a molecule having protein-stabilizing action, such as polyethylene glycol (PEG). An anti-p53 antagonist antibody can be produced using p53 or a partial peptide thereof as an antigen, by a method of antibody or anti-serum production known per se. As examples of known anti-p53 antagonist antibodies, PAb1801 (Oncogene Science Ab-2) and DO-1 (Oncogene Science Ab-6) (Gire and Wynford-Thomas, *Mol. Cell. Biol.*, 18, 1611-1621 (1998)) and the like can be mentioned. A nucleic acid that encodes an anti-p53 antagonist antibody can be isolated from a hybridoma that produces an anti-p53 monoclonal antibody by a conventional method. The H-chain and L-chain genes obtained may be joined together to prepare a nucleic acid that encodes a single-chain antibody.

As another substance that inhibits the function of the p53 protein, an anti-p21 antagonist antibody or a nucleic acid that encodes the same can be mentioned. An anti-p21 antagonist antibody and a nucleic acid that encodes the same can also be prepared as with the aforementioned anti-p53 antagonist antibody and nucleic acid that encodes the same.

Still another substance that inhibits the function of the p53 protein is a decoy nucleic acid comprising a consensus sequence of p53-responsive element (see for example Nat. Genet., 1(1): 45-49 (1992)). Such a nucleic acid can be synthesized on the basis of the aforementioned nucleotide sequence information using an automated DNA/RNA synthesizer. Alternatively, such a decoy nucleic acid is commercially available (e.g., p53 transcription factor decoy (GeneDetect.com)).

An anti-p53 antagonist antibody or an anti-p21 antagonist antibody, and a nucleic acid that encodes the antibody can be introduced into a cell with the method described in the statement of a dominant negative mutant of p53, and a nucleic acid that encodes the mutant, respectively. The aforementioned decoy nucleic acid can be introduced into a cell by lipofection method and the like.

Meanwhile, as examples of substances that inhibit the expression of the p53 gene, siRNAs or shRNAs against p53, vectors that express an siRNA or shRNA against p53, antisense nucleic acids against p53 and ribozymes against p53, and the like can be mentioned, and siRNAs and shRNAs against p53 and vectors that express an siRNA or an shRNA are preferable.

(D6) siRNA and shRNA Against p53

An siRNA against p53 can be designed on the basis of the mouse or human p53 cDNA sequence information, in accordance with, for example, the rules proposed by Elbashir et al. (*Genes Dev.*, 15, 188-200 (2001)). The target sequence for the siRNA is, as a general rule, AA+(N)$_{19}$, but may be AA+(N)$_{21}$ or NA+(N)$_{21}$. The 5' end of the sense strand need not to be AA. Although the position of the target sequence is not particularly limited, it is desirable that the target sequence be selected from a region other than 5'-UTR, about 50 bases from the start codon, or 3'-UTR. The GC content of the target sequence is also not particularly limited, but the content is preferably about 30 to about 50%; a sequence with no irregularity in GC distribution and with only a few repeats is desirable. When a polIII promoter is used as a promoter in designing a vector that expresses an siRNA or shRNA, a sequence of 4 or more T or A bases in succession should not be chosen, so as to prevent polymerase transcription from ceasing.

The target sequence candidates selected on the basis of the above-described rules are examined for homology to sequences of 16-17 bases in succession in mRNAs other than the target, using a homology search software program such as BLAST (http://www.ncbi.nlm.nih.gov/BLAST/), so as to confirm the specificity of the target sequences selected. For the target sequences for which the specificity has been confirmed, a double-stranded RNA consisting of a sense strand having a 3'-terminal overhang of TT or UU in 19-21 bases after AA (or NA) and an antisense strand having a sequence complementary to the 19-21 bases and a 3'-terminal overhang of TT or UU, is designed as an siRNA. Also, an shRNA can be designed by choosing as appropriate an optionally chosen linker sequence capable of forming a loop structure (for example, about 8-25 bases), and ligating the aforementioned sense strand and antisense strand via the linker sequence.

Sequences of siRNAs and/or shRNAs can be searched for using search software programs available at no cost on various websites. Examples of such sites include, but are not limited to, the siRNA Target Finder (http://www.ambion.com/jp/techlib/misc/siRNA_finder.html) and insert design tool for pSilencer™ Expression Vector (http://www.ambion.com/jp/techlib/misc/psilencer_converter.htm 1), both provided by Ambion, and GeneSeer (http://codex.cshl.edu/ scripts/newsearchhairpin.cgi), provided by RNAi Codex; and similar search is possible on the websites of QIAGEN, Takara Bio, SiSearch, Dharmacon, Whitehead Institute, Invitrogen, Promega and the like.

An siRNA against p53 can be prepared by synthesizing a sense strand oligonucleotide and antisense strand oligonucleotide designed as described above using an automated DNA/RNA synthesizer separately, and, for example, denaturing the oligonucleotides in an appropriate annealing buffer solution at about 90 to about 95° C. for about 1 minute, thereafter annealing the same at about 30 to about 70° C. for about 1 to about 8 hours. An shRNA against p53 can be prepared by synthesizing oligonucleotides having an shRNA sequence, designed as described above, using an automated DNA/RNA synthesizer, and allowing the same to self-anneal as described above.

Although the nucleotide molecules that constitute the siRNA and shRNA may be naturally occurring RNAs, the molecules can comprise various chemical modifications in order to increase the stability (chemical and/or against enzyme) or specific activity (affinity for mRNA). For example, to prevent degradation by hydrolases such as nuclease, the phosphoric acid residue (phosphate) of each nucleotide that constitutes the antisense nucleic acid can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —OR (R represents, for example, $CH_3$(2'-O-Me), $CH_2CH_2OCH_3$(2'-O-MOE), $CH_2CH_2NHC(NH)NH_2$, $CH_2CONHCH_3$, $CH_2CH_2CN$ or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl and the like can be mentioned.

Regarding the conformation of the sugar moiety of RNA, two types are dominant: C2'-endo (S type) and C3'-endo (N type); in a single-stranded RNA, the conformation of the sugar moiety occurs in an equilibrium of both, but when a double strand is formed, the conformation is fixed at the N type. Therefore, BNA (LNA) (Imanishi, T. et al., *Chem. Commun.*, 1653-9, 2002; Jepsen, J. S. et al., *Oligonucleotides*, 54, 130-46, 2004) and ENA (Morita, K. et al., *Nucleosides Nucleotides Nucleic Acids*, 22, 1619-21, 2003), which are RNA derivatives wherein the conformation of the sugar moiety is fixed at the N type by bridging the 2' oxygen and 4' carbon so as to confer strong bindability to the target RNA, can also be used preferably.

However, because replacing all ribonucleoside molecules in a naturally occurring RNA with modified type molecules can lead to the loss of RNAi activity, it is necessary to introduce modified nucleosides to the minimum possible extent that allows the RISC complex to function.

An siRNA against p53 can also be purchased from, for example, Ambion (e.g., Ambion Cat# AM16708, an siRNA ID#69659, 69753, 69843, 187424, 187425, 187426), Santa Cruz (e.g., Santa Cruz Cat# sc-29436, 44219) and the like.

An siRNA and shRNA against human p53 can also be designed and synthesized using one of the aforementioned search software programs, by inputting the sequence of human p53' cDNA shown by Refseq. No. (NM_000546) and the like as a query, or can also be purchased from Ambion and the like. Specifically, the shRNA against p53 described in *Science*, 296, 550-553 (2002), and the like can be mentioned.

Contact of an siRNA or shRNA against p53 with a somatic cell can be achieved by, as in the case of plasmid DNA, introducing the nucleic acid into the cell using the liposome method, polyamine method, electroporation method, beads method and the like. The method using a cationic liposome is the most common and offers high transfer efficiency. In addition to common transfection reagents such as Lipofectamine-2000 and Oligofectamine (Invitrogen), for example, transfer reagents suitable for introduction of an siRNA, such as the GeneEraser™ siRNA transfection reagent (Stratagene), are also commercially available.

(D7) Vectors that Express siRNA or shRNA Against p53

Vectors that express an siRNA are available in the tandem type and the stem loop (hairpin) type. The former is the type in which an expression cassette for a sense strand of an siRNA and an expression cassette for an antisense strand are ligated tandem, each strand being expressed in the cell and undergoing annealing to form a double-stranded siRNA (dsRNA). Meanwhile, the latter is the type in which an expression cassette for an shRNA is inserted into a vector, the shRNA being expressed in the cell and undergoing processing by a dicer to form a dsRNA. Although a polII promoter (for example, immediate-early promoter of CMV) may be used as the promoter, it is common practice to use a polIII promoter in order to allow the accurate transcription of short RNA. As the polIII promoter, mouse and human U6-snRNA promoters, human H1-RNase P RNA promoter, human valine-tRNA promoter and the like can be mentioned. As a transcription termination signal, a sequence of 4 or more T residues in succession is used.

The siRNA or shRNA expression cassette thus constructed is then inserted into a plasmid vector or a viral vector. Such vectors that can preferably be utilized are the same as those mentioned above in relation to nucleic acids which are nuclear reprogramming substances (reprogramming genes) (viral vectors such as retrovirus, lentivirus, adenovirus, adeno-associated virus, herpesvirus, and Sendai virus; animal cell expression plasmids; episomal vectors and the like). A vector, like reprogramming genes, can be chosen as appropriate according to the intended use of the iPS cell obtained. Alternatively, as an expression vector that encodes the shRNA against p53, a viral vector of retrovirus or the like, a plasmid vector, an episomal vector and the like, prepared on the basis of a commercially available plasmid (for example, pMKO.1-puro p53 shRNA2: #10672, commercially available from Addgene, and the like) or the like can also be used. The aforementioned Cre-loxP system or piggyBac transposon system can also be utilized as required.

Contact of a vector that expresses the siRNA or shRNA against p53 with a somatic cell is achieved by introducing a plasmid vector, episomal vector or viral vector prepared as described above into the cell. These transfections can be achieved by the same techniques as those described above with respect to reprogramming genes.

(D8) Other Substances

As other substances that inhibit the expression of the p53 gene, antisense nucleic acids and ribozymes against p53 can be mentioned.

The antisense nucleic acid may be a DNA or an RNA, or a DNA/RNA chimera. When the antisense nucleic acid is a DNA, an RNA:DNA hybrid formed by a target RNA and the antisense DNA is capable of being recognized by endogenous RNase H to cause selective degradation of the target RNA. Therefore, in the case of an antisense DNA that directs the degradation by RNase H, the target sequence may be not only a sequence in p53 mRNA, but also a sequence in the intron region of the primary transcript of the p53 gene. The length of the target region for the antisense nucleic acid is not particularly limited, as far as hybridization of the antisense nucleic acid results in an inhibition of the translation into the p53 protein; the target region may be the entire sequence or a partial sequence of p53 mRNA, and may be a sequence of about 15 bases for the shortest, or of the entire sequence of the mRNA or primary transcript for the longest. Considering the ease of synthesis, antigenicity, transferability into cells and other issues, an oligonucleotide consisting of about 15 to about 40 bases, particularly about 18 to about 30 bases, is preferable. Positions of the target sequence include, but are not limited to, 5'- and 3'-UTR, vicinities of the start codon and the like.

A ribozyme refers to an RNA possessing an enzyme activity to cleave a nucleic acid in the narrow sense, and is herein understood to be used as a concept encompassing a DNA, as far as it possesses sequence-specific nucleic acid cleavage activity. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends adjoining to the hammerhead structure portion (about 10 bases in total) be a sequence complementary to the desired cleavage site of the mRNA.

An antisense nucleic acid or a ribozyme can be synthesized using an automated DNA/RNA synthesizer. The nucleotide molecules that constitute them may also have the same modifications as those described above for siRNA, so as to increase the stability, specific activity and the like.

Alternatively, the antisense nucleic acid or ribozyme can also be used in the form of a nucleic acid that encodes the same, as in the case of siRNA.

A functional inhibitor of p53 needs to be brought into contact with a somatic cell in a way sufficient to inhibit the p53 function in the step of somatic cell nuclear reprogramming. As far as this requirement is met, the nuclear reprogramming substance and the functional inhibitor of p53 may be brought into contact with the somatic cell simultaneously, or either one may be brought into contact in advance. In a mode of embodiment, for example, when the nuclear reprogramming substance is a nucleic acid that encodes a proteinous factor, and the functional inhibitor of p53 is a chemical inhibitor, the former involves a given length of time lag from the transfection treatment to the mass-expression of the proteinous factor, whereas the latter is capable of rapidly inhibiting the p53 function, so that after the cell is cultured for a given length of time after the transfection treatment, the chemical inhibitor of p53 can be added to the medium. In another mode of embodiment, for example, when the nuclear reprogramming substance and the functional inhibitor of p53 are used in the form of viral vectors, plasmid vectors, episomal vectors and the like, both may be simultaneously introduced into the cell.

(E) iPS Cell Establishment Efficiency Improvers

In addition to the above-described reprogramming factors and the like, other commonly known iPS cell establishment efficiency improvers may be brought into contact with the somatic cell, whereby a further increase in the iPS cell establishment efficiency is expected. Examples of such iPS cell establishment efficiency improvers include, but are not limited to, histone deacetylase (HDAC) inhibitors [e.g., low-molecular inhibitors such as valproic acid (VPA) (*Nat. Biotechnol.*, 26(7): 795-797 (2008)), trichostatin A, sodium butyrate, MC1293, and M344, nucleic acid-based expression inhibitors such as siRNAs and shRNAs against HDAC (e.g., HDAC1 siRNA Smartpool® (Millipore), HuSH 29 mer shRNA Constructs against HDAC1 (OriGene) and the like), and the like], G9a histone methyltransferase inhibitors [e.g., low-molecular inhibitors such as BIX-01294 (Cell Stem Cell, 2: 525-528 (2008)), nucleic acid-based expression inhibitors such as siRNAs and shRNAs against G9a (e.g., G9a siRNA (human) (Santa Cruz Biotechnology) and the like) and the like], L-calcium channel agonists (e.g., Bayk8644) [*Cell Stem Cell*, 3, 568-574 (2008)], UTF1 [*Cell Stem Cell*, 3, 475-479 (2008)], Wnt Signaling (e.g., soluble Wnt3a) [*Cell Stem Cell*, 3, 132-135 (2008)], 2i/LIF [2i is an inhibitor of mitogen-activated protein kinase signaling and glycogen synthase kinase-3, *PloS Biology*, 6(10), 2237-2247 (2008)], ES cell-specific miRNAs [e.g., miR-302-367 cluster (Mol. Cell. Biol. doi:10.1128/MCB.00398-08, WO2009/075119), miR-302 (RNA (2008) 14: 1-10), miR-291-3p, miR-294 and miR-295 (for these three, see Nat. Biotechnol. 27: 459-461 (2009))] and the like. As mentioned above, the nucleic acid-based expression inhibitors may be in the form of expression vectors harboring a DNA that encodes an siRNA or shRNA.

Among the constituents of the aforementioned nuclear reprogramming substances, SV40 large T antigen and the like, for example, can also be included in the scope of iPS cell establishment efficiency improvers because they are deemed not essential, but auxiliary, factors for somatic cell nuclear reprogramming. In the situation of the mechanisms for nuclear programming remaining unclear, the auxiliary factors, which are not essential for nuclear reprogramming, may be conveniently considered as nuclear reprogramming substances or iPS cell establishment efficiency improvers. Hence, because the somatic cell nuclear reprogramming process is understood as an overall event resulting from contact of nuclear reprogramming substance(s) and iPS cell establishment efficiency improver(s) with a somatic cell, it seems unnecessary for those skilled in the art to always distinguish between the nuclear reprogramming substance and the iPS cell establishment efficiency improver.

Contact of these other iPS cell establishment efficiency improvers with a somatic cell can be achieved as described above with respect to functional inhibitors of p53 for each of three cases: (a) the improver is a proteinous factor, (b) the improver is a nucleic acid that encodes the proteinous factor, and (c) the improver is a low-molecular compound.

The other iPS cell establishment efficiency improvers may be brought into contact with a somatic cell simultaneously with a nuclear reprogramming substance, or either one may be contacted in advance, as far as the efficiency of establishment of iPS cells from the somatic cell is significantly improved, compared with the absence of the improver; according to the properties of the substance, the substance can be brought into contact with the somatic cell at the same timing as that described above in relation to a is functional inhibitor of p53.

(F) Improving Establishment Efficiency by Culture Conditions iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with the nuclear reprogramming substance, or at the same time as the contact, or after the contact, it is preferable, for example, that the culture under hypoxic conditions be started just after the somatic cell is contacted with the nuclear reprogramming substance, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency improver and the like.

(G) Culture Condition and First Selection of iPS Cell

After being contacted with nuclear reprogramming substances and iPS cell establishment efficiency improver if required, the cell can be cultured under conditions suitable for the cultivation of, for example, ES cells. In the case of mouse cells, the cultivation is carried out with the addition of Leukemia Inhibitory Factor (LIF) as a differentiation suppressor to an ordinary medium. Meanwhile, in the case of human cells, it is desirable that basic fibroblast growth factor (bFGF) and/or stem cell factor (SCF) be added in place of LIF. Usually, the cells are cultured in the co-presence of mouse embryo-derived fibroblasts treated with radiation or an antibiotic to terminate the cell division thereof, as feeder cells. Mouse embryonic fibroblasts in common use as feeders include the STO cell line (ATCC CRL-1503) and the like; for induction of an iPS cell, the SNL cell generated by stably integrating the neomycin resistance gene and the LIF gene in the STO cell (SNL76/7 STO cell; ECACC 07032801) [McMahon, A. P. & Bradley, A. Cell 62, 1073-1085 (1990)] and the like are commonly used. However, in the present invention, it is more preferable to use a mouse embryonic primary fibroblast (MEF) because its use offers a further improvement of human iPS cell establishment efficiency. Mitomycin C-treated MEFs are commercially available from Millipore and ReproCELL. Co-culture with these feeder cells may be started before contact of the nuclear reprogramming substance, at the time of the contact, or after the contact (e.g., 1-10 days later).

A candidate colony of iPS cells can be selected by a method with drug resistance and reporter activity as indicators, and also by a method based on visual examination of morphology. As an example of the former, a colony positive for drug resistance and/or reporter activity is selected using a recombinant somatic cell wherein a drug resistance gene and/or a reporter gene is targeted to the locus of a gene highly expressed specifically in pluripotent cells (e.g., Fbx15, Nanog, Oct3/4 and the like, preferably Nanog or Oct3/4). Examples of such recombinant somatic cells include MEFs from a mouse having the βgeo (which encodes a fusion protein of β-galactosidase and neomycin phosphotransferase) gene knocked-in to the Fbx15 locus [Takahashi & Yamanaka, Cell, 126, 663-676 (2006)], MEFs from a transgenic mouse having the green fluorescent protein (GFP) gene and the puromycin resistance gene integrated in the Nanog locus [Okita et al., Nature, 448, 313-317 (2007)] and the like. Meanwhile, examples of the method of selecting candidate colonies based on visual examination of morphology include the method described by Takahashi et al. in Cell, 131, 861-872 (2007). Although the method using reporter cells is convenient and efficient, it is desirable from the viewpoint of safety that colonies be selected by visual examination when iPS cells are prepared for the purpose of human treatment.

The identity of the cells of a selected colony as iPS cells can be confirmed by positive responses to a Nanog (or Oct3/4) reporter (puromycin resistance, GFP positivity and the like) as well as by the formation of a visible ES cell-like colony, as described above. However, to ensure higher accuracy, it is possible to perform tests such as alkaline phosphatase staining, analyzing the expression of various ES-cell-specific genes, and transplanting the cells selected to a mouse to confirm the formation of teratomas.

III. Methods of Differentiation Induction

Herein, "differentiation induction" is understood to include not only differentiation into particular organ cells and progenitor cells thereof, but also differentiation into cell populations including a wide variety of cell types such as endodermal cells, mesodermal cells and ectodermal cells. Organs targeted in the present invention include, but are not limited to, the skin, blood vessels, cornea, kidney, heart, liver, umbilical cord, intestine, nerves, lung, placenta, pancreas, brain, limb peripheries, retina and the like. Any method of differentiation induction obvious to those skilled in the art can be used; examples include the method of induction of differentiation into nerve stem cells described in JP-A-2002-291469, the method of induction of differentiation into pancreatic stem-like cells described in JP-A-2004-121165, and the method of induction of differentiation into hematopoietic cells described in JP-T-2003-505006. In addition, methods of induction of differentiation by formation of embryoid are exemplified by the method described in JP-T-2003-523766 and the like.

A preferred method of differentiation induction in the present invention involves the use of retinoic acid (RA). Specifically, cells are cultured with the addition of RA to a medium for pluripotent stem cells at concentrations of 50 nM to 1000 nM. The RA concentration is preferably between 50 nM or more (e.g., 100 nM, 150 nM, 200 nM, 250 nM or 300 nM) and 1000 nM or less (e.g., 900 nM, 800 nM, 700 nM, 600 nM, 500 nM or 400 nM). More preferably, the concentration is 300 nM or 1000 nM. Examples of useful media include, but are not limited to, a minimal essential medium (MEM) containing about 5 to 20% fetal calf serum, Dulbecco's modified Eagle medium (DMEM), RPMI1640 medium, 199 medium, F12 medium, mixtures thereof and the like. These media may be supplemented with nonessential amino acids, nucleosides, 2-mercaptoethanol and the like as appropriate. Before adding RA, preparatory cultivation may be performed using the above-described medium for 1 day. The cell density of the pluripotent stem cells used for differentiation may be 100000 to 250000 cells/10 cm-dish (e.g., 250000 cells/10 cm-dish, 200000 cells/10 cm-dish, 150000 cells/10 cm-dish or 100000 cells/10 cm-dish), and is preferably 200000 cells/10 cm-dish. Although the duration of cultivation using an RA-supplemented medium is not particularly limited, the length may be 2 to 10 days (e.g., 10 days, 8 days, 6 days, 4 days, 2 days), particularly preferably 4 days.

IV. Shifting to Conditions for Maintaining Undifferentiated State

Subsequently, the cells as differentiated above are again cultured under conditions for maintaining undifferentiated state to detect differentiation resistance. In the present invention, the conditions for maintaining undifferentiated state are conditions under which pluripotent stem cells can proliferate while retaining pluripotency, and are exemplified by conditions under which the cells are cultured along with feeder cells. Useful media include, but are not limited to, a minimal essential medium (MEM) containing about 5 to 20% fetal calf serum, Dulbecco's modified Eagle medium (DMEM), RPMI1640 medium, 199 medium, F12 medium, or combinations thereof, supplemented with nonessential amino acids, nucleosides, 2-mercaptoethanol and the like. In this operation, cytokines such as LIF and bFGF, 2i [an inhibitor of mitogen-activated protein kinase signalling and glycogen synthase kinase-3, PloS Biology, 6(10), 2237-2247 (2008)] and the like may be added to the medium as appropriate. It is preferable that the medium be replaced with a fresh supply every 2 days.

In shifting from differentiation conditions to undifferentiation conditions, the cells may be detached from the dish and reseeded. In this reseeding, viable cells alone may be selected. Although the method of selecting viable cells is not particularly limited, this selection can be achieved by staining the cells with propidium iodide (PI), and separating and purifying non-stained cells by FACS and the like.

The duration of cultivation under undifferentiation conditions may be of any length allowing examination of colonies, and is preferably 10 days, 9 days, 8 days, 7 days, 6 days or 5 days, more preferably 7 days.

Although the cell density during cultivation of the cells induced to differentiate is not particularly limited, the cell density may be 100000 to 250000 cells/10 cm-dish (e.g., 250000% cells/10 cm-dish, 200000 cells/10 cm-dish, 150000 cells/10 cm-dish or 100000 cells/10 cm-dish), preferably 200000 cells/10 cm-dish.

In this operation, the pluripotent stem cells may be continued to be cultured under undifferentiation conditions, without differentiation induction, to obtain a control. In this case, to prevent the excess generation of colonies, the cells may be seeded at a cell density 1/15 to 1/5 (e.g., 1/15, 1/10, 1/5) of the cell density after differentiation induction of a sample pluripotent stem cell; the cell density is preferably 1/10.

V. Method of Detecting Generation of Undifferentiated Cells

The generation of undifferentiated cells after re-cultivation under undifferentiation conditions after differentiation induction as described above can be detected on the basis of a property specific for undifferentiated cells. Such specific properties include formation of a colony, expression of a non-differentiation-specific antigen, expression of a non-differentiation-specific gene and the like. Here, a non-differentiation-specific antigen is selected from the group consisting of SSEA-1, SSEA-3, SSEA-4, Tra1-60 and Tra1-81, which are not to be construed as limiting. In this context, SSEA-1 is not detected in undifferentiated cells in humans; SSEA-3, SSEA-4, Tra1-60 and Tra1-81 are suitably used in place of SSEA-1. Examples of non-differentiation-specific genes are given in WO2007/069666.

From the viewpoint of the ability to ensure sufficient sensitivity and specificity with simple procedures, it is preferable that the generation of undifferentiated cells be detected by examining for the formation of a colony. Colonies may be counted by any method, for example, counting under a microscope, and evaluation is performed on the basis of the counts. This measurement may be made mechanically or visually. Meanwhile, cells expressing a non-differentiation-specific antigen or gene can be evaluated as a number of cells expressing the antigen or gene using FACS.

VI. Methods of Sorting Pluripotent Stem Cells (A) Method of Selection by Absolute Evaluation It is desirable that the number of undifferentiated cells detected after re-cultivation under undifferentiation conditions after differentiation induction as described above be evaluated as a relative value to the cell count as of the start of cultivation. Here, the number to be evaluated is exemplified by the number of colonies formed, or the number of cells expressing a non-differentiation-specific antigen or gene, per 200000 cells induced to differentiate.

In sorting pluripotent stem cells by differentiation resistance, a pluripotent stem cell wherein the value of undifferentiated cells detected is not more than the value of undifferentiated cells generated from a control pluripotent stem cell known to exhibit differentiation resistance (control generation value; hereinafter, simply abbreviated to control value) is selected as a pluripotent stem cell that does not exhibit differentiation resistance. Here, the control value used may be a value previously determined so that the values of sensitivity and/or specificity shown in Table 1 will be 0.9 or more, preferably 0.95 or more, more preferably 0.99 or more, wherein Table 1 has been generated with values of the number of undifferentiated cells obtained by culturing an available optionally chosen pluripotent stem cell line known to exhibit differentiation resistance under undifferentiation conditions after differentiation induction. Particularly preferably, the values of sensitivity and specificity are both 1. Here, the fact that the sensitivity and specificity values are both 1 means that the control value is ideal in that there are absolutely no false-positive responses and false-negative responses. The aforementioned available optionally chosen cell line is exemplified by ES cell lines.

TABLE 1

| | Number of pluripotent stem cell lines not exhibiting differentiation resistance | Number of pluripotent stem cell lines exhibiting differentiation resistance |
|---|---|---|
| Number of cell lines having higher | A | C |

TABLE 1-continued

|  | Number of pluripotent stem cell lines not exhibiting differentiation resistance | Number of pluripotent stem cell lines exhibiting differentiation resistance |
|---|---|---|
| values than control value |  |  |
| Number of cell lines having lower values than control value | B | D |
|  | Sensitivity = B/(A + B) | Specificity = C/(C + D) |

When differentiation induction is performed in the presence of 300 nM of RA, the control value is preferably, for example, 600 colonies or less (e.g., 500, 400, 300, 200 or 100 colonies) per 200000 cells induced to differentiate. More preferably, the control value is 300 colonies, still more preferably 250 colonies, particularly preferably 216 colonies. Meanwhile, when differentiation induction is performed in the presence of 1000 nM of RA, preferred control values include 50 colonies or less (e.g., 40, 30, 20, 10 or 5 colonies) per 200000 cells induced to differentiate. The control value is more preferably 20 colonies, still more preferably 15 colonies, particularly preferably 12 colonies. As stated above, the control value can be changed according to differentiation induction conditions.

(B) Method of Selection by Relative Evaluation

Pluripotent stem cells that do not exhibit differentiation resistance can be selected by calculating the ratio of the number of colonies formed or the number of undifferentiated cells, obtained by culturing a pluripotent stem cell under undifferentiation conditions after differentiation induction, relative to the number of colonies formed or the number of undifferentiated cells, obtained by culturing the cell while in the undifferentiated state. For example, a pluripotent stem cell wherein the above-described ratio is not more than the ratio in a control pluripotent stem cell known to exhibit differentiation resistance (hereinafter, control ratio) can be selected as a pluripotent stem cell that does not exhibit differentiation resistance. Here, the control ratio used may be a value previously determined so that the values of sensitivity and/or specificity shown in Table 2 will be 0.9 or more, preferably 0.95 or more, more preferably 0.99 or more, wherein Table 2 has been generated with values of the ratio obtained by culturing an available optionally chosen pluripotent stem cell line known to exhibit differentiation resistance. Particularly preferably, the values of sensitivity and specificity are both 1. Here, the fact that the sensitivity and specificity values are both 1 means that the control ratio is ideal in that there are absolutely no false-positive responses and false-negative responses. The aforementioned available optionally chosen cell line is exemplified by ES cell lines.

TABLE 2

|  | Number of pluripotent stem cell lines not exhibiting differentiation resistance | Number of pluripotent stem cell lines exhibiting differentiation resistance |
|---|---|---|
| Number of cell lines having higher values than control ratio | A | C |
| Number of cell lines having lower values than control ratio | B | D |
|  | Sensitivity = B/(A + B) | Specificity = C/C + D |

When differentiation induction is performed in the presence of 300 nM of RA, the control ratio is preferably 5% or less (e.g., 4%, 3%, 2%, 1%, 0.9%, 0.8%, 0.7%, 0.6%, 0.5% or 0.4%). The control ratio is more preferably 1%, still more preferably 0.6%, particularly preferably 0.58%. Meanwhile, when differentiation induction is performed in the presence of 1000 nM of RA, the control ratio is preferably 0.1% or less (e.g., 0.09%, 0.08%, 0.07%, 0.06%, 0.05%, 0.04%, 0.03%, 0.02% or 0.01%). More preferably, the ratio is 0.06%, still more preferably 0.055%, particularly preferably 0.052%.

The present invention is hereinafter described in further detail by means of the following examples, to which, however, the invention is never limited.

EXAMPLE

Cells

Cultivation of ES cells (RF8, 1A2) and establishment and cultivation of the sample iPS cells shown in Table 3 were performed by the conventional methods described below [Takahashi K and Yamanaka S, Cell 126 (4), 663, 2006; Okita K, et al., Nature 448 (7151), 313, 2007; Nakagawa M, et al., Nat Biotechnol 26 (1), 101, 2008; Aoi, T. et al., Science 321, 699-702, 2008]. 212C6 (undifferentiated clone), a cell line established from cells that expressed Nanog, a gene specific for the undifferentiated state, even after differentiation induction of 212C6 by the method described by Miura K. et al., in *Nat. Biotechnol.*, 27: 743-745 (2009), was used as a cell line exhibiting differentiation resistance.

TABLE 3

| iPS clone's name | Origin | Factor |
|---|---|---|
| 178B5 | MEF | Oct3/4, Sox2, Klf4 |
| 335D1 | TTF | Oct3/4, Sox2, Klf4 |
| 38C2 | MEF | Oct3/4, Sox2, Klf4, c-Myc |
| 38D2 | MEF | Oct3/4, Sox2, Klf4, c-Myc |
| 238C2 | Hep | Oct3/4, Sox2, Klf4 |
| 212B2 | TTF | Oct3/4, Sox2, Klf4, c-Myc |
| 212C6 | TTF | Oct3/4, Sox2, Klf4, c-Myc |
| 212D1 | TTF | Oct3/4, Sox2, Klf4 |
| 256D4 | TTF | Oct3/4, Sox2, Klf4 |

Method of Cultivation and Colony Counting

Figure 2:
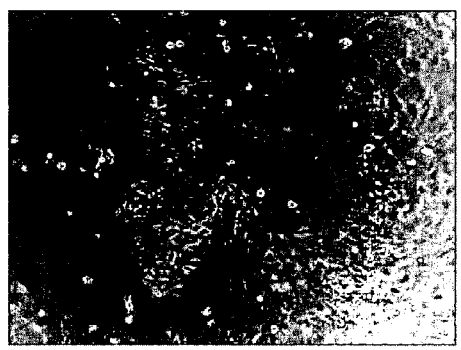
FIG. 2 shows images of cells of the ES cell clone 1A2 (A) and the three iPS cell clones 335D1 (B), 212C6 (C) and 256D4 (D), obtained after differentiation induction by treatment with 300 nM retinoic acid (RA) (day 5).
Figure 2:
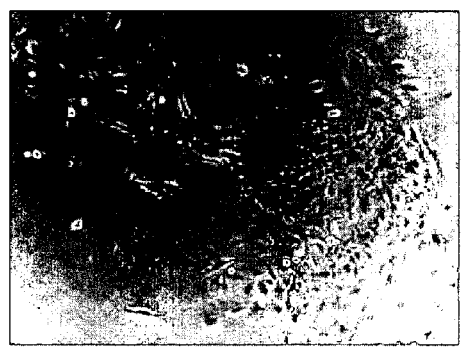
Figure 2:
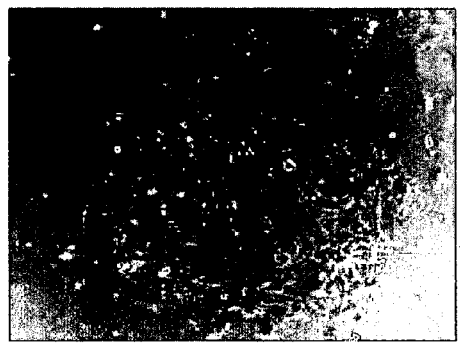
Figure 2:
Figure 3:
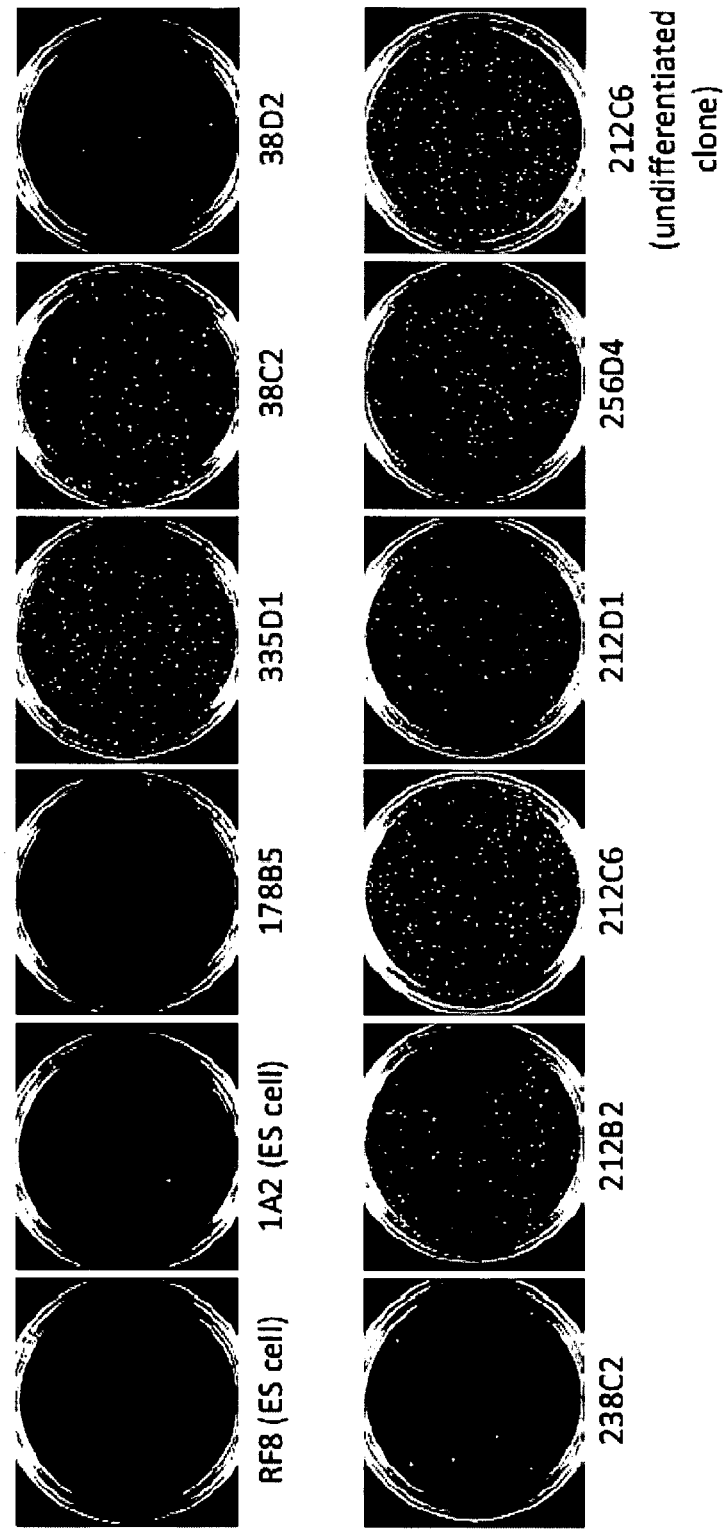
FIG. 3 shows images of cells obtained after ES cells and iPS cells were cultured under conditions for maintaining the undifferentiated state after differentiation induction with 300 nM RA (day 12).
Figure 4:
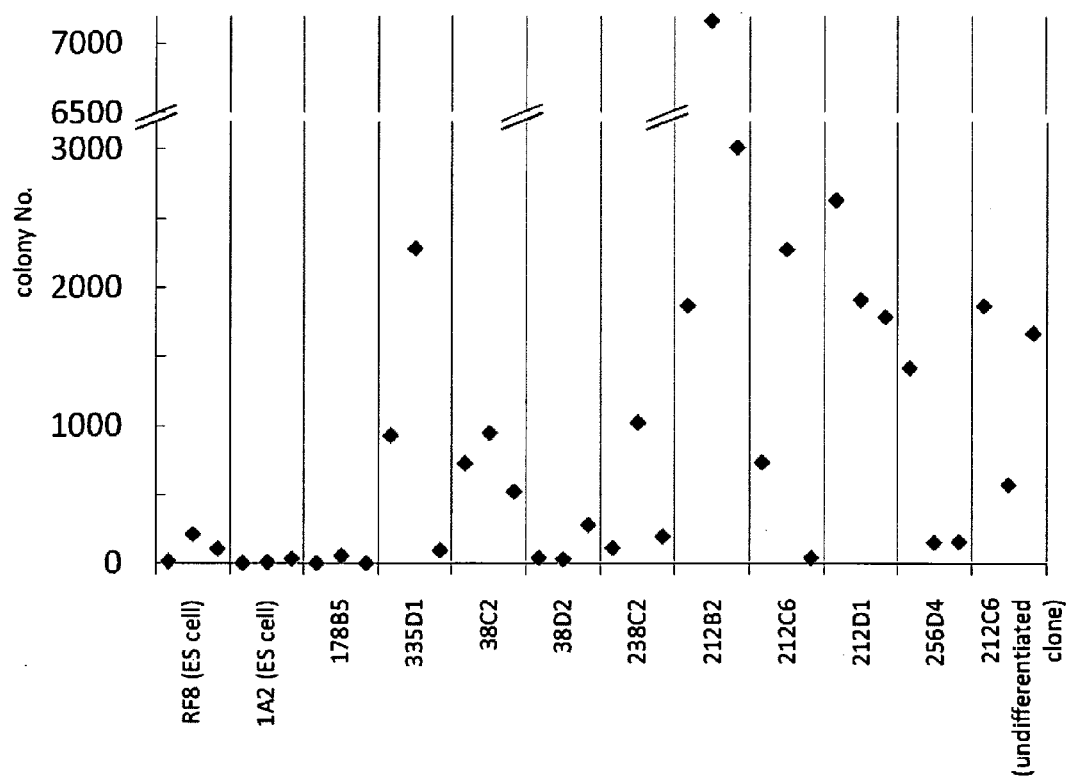
FIG. 4 shows the results of counting colonies formed from each cell line obtained after cultivation under conditions for maintaining the undifferentiated state (day 12) after differentiation induction with 300 nM RA. The axis of ordinates indicates the number of colonies formed from 200000 cells induced to differentiate. Three experiments were performed on each cell line; all results are shown.

The operating scheme used in this example is shown in FIG. 1. Specifically, 200000 ES cells or iPS cells were seeded to a gelatin-coated 100 mm dish, and cultured using an LIF-free medium for ES cells (day 0). One day later, the cells were cultured using the following three different media (LIF-containing medium, medium containing 300 nM RA, and medium containing 1000 nM RA) (day 1). Two days later, each medium was replaced with a fresh supply of the same (day 3). Representative photomicrographs of cells induced to differentiate (1A2, 335D1, 212C6 and 256D4) that were taken 2 more days later are shown in FIG. 2. Next, the cells were detached from the dish and stained with PI; viable cells were separated by FACS Aria, out of which 20000 viable cells (in case of the LIF-containing medium) or 200000 viable cells (in case of the RA-containing media) were seeded to a 100 mm dish in which mitomycin C-treated SNL cells had been cultured as feeder cells. In this operation, the LIF-containing medium was used (day 5). The following day (day 6), 2 days later (day 8), and 2 more days later (day 10), the medium was replaced with a fresh supply of the same. Two days after final medium exchange, the colonies formed were counted (day 12). Photomicrographs of cells at the time of colony counting are shown in FIG. 3. The results of colony counting are shown in Table 4 and FIG. 4. These results demonstrated that of the 9 sample iPS cell lines (178B5, 335D1, 38C2, 38D2, 238C2, 212B2, 212C6, 212D1 and 256D4), only 178B5 was an iPS cell that does not exhibit differentiation resistance.

TABLE 4

| Clone name | Experiment No. | Colony No. (per 20000 cells) LIF | Colony No. (per 200000 cells) RA: 300 nM | Colony No. (per 200000 cells) RA: 1000 nM | Ratio (%) (RA treated colony No. vs LIF colony No. per 200000 cells) RA: 300 nM | Ratio (%) (RA treated colony No. vs LIF colony No. per 200000 cells) RA: 1000 nM |
|---|---|---|---|---|---|---|
| RF8 (ES cell) | 1 | 4484 | 19 | 0 | 0.042372881 | 0 |
| | 2 | 3726 | 216 | 7 | 0.579710145 | 0.018786903 |
| | 3 | 2128 | 110 | 11 | 0.516917293 | 0.051691729 |
| | 4 | — | — | 5 | — | — |
| | 5 | — | — | 14 | — | — |
| 1A2 (ES cell) | 1 | 2664 | 6 | 0 | 0.022522523 | 0 |
| | 2 | 1792 | 13 | 3 | 0.072544643 | 0.016741071 |
| | 3 | 2328 | 38 | 12 | 0.163230241 | 0.051546392 |
| | 4 | — | — | 0 | — | — |
| | 5 | — | — | 2 | — | — |
| 178B5 | 1 | 1304 | 7 | 0 | 0.053680982 | 0 |
| | 2 | 1572 | 60 | 4 | 0.381679389 | 0.025445293 |
| | 3 | 688 | 5 | 0 | 0.072674419 | 0 |
| | 4 | — | — | 1 | — | — |
| | 5 | — | — | 0 | — | — |
| 335D1 | 1 | 1096 | 932 | 704 | 8.503649635 | 6.423357664 |
| | 2 | 2072 | 2284 | 756 | 11.02316602 | 3.648648649 |
| | 3 | 3428 | 99 | 144 | 0.288798133 | 0.420070012 |
| | 4 | — | — | 515 | — | — |
| | 5 | — | — | 675 | — | — |
| 38C2 | 1 | 1160 | 728 | 112 | 6.275862069 | 0.965517241 |
| | 2 | 2788 | 948 | 508 | 3.400286944 | 1.822094692 |
| | 3 | 1024 | 524 | 57 | 5.1171875 | 0.556640625 |
| | 4 | — | — | 2 | — | — |
| | 5 | — | — | 122 | — | — |
| 38D2 | 1 | 320 | 45 | 63 | 1.40625 | 1.96875 |
| | 2 | 1396 | 34 | 636 | 0.243553009 | 4.555873926 |
| | 3 | 680 | 284 | 30 | 4.176470588 | 0.441176471 |
| | 4 | — | — | 12 | — | — |
| | 5 | — | — | 22 | — | — |
| 238C2 | 1 | 728 | 116 | 6 | 1.593406593 | 0.082417582 |
| | 2 | 544 | 1024 | 8 | 18.82352941 | 0.147058824 |
| | 3 | 412 | 200 | 126 | 4.854368932 | 3.058252427 |
| | 4 | — | — | 25 | — | — |
| | 5 | — | — | 34 | — | — |
| 212B2 | 1 | 1488 | 1872 | 1442 | 12.58064516 | 9.690860215 |
| | 2 | 1172 | 7164 | 2040 | 61.12627986 | 17.40614334 |
| | 3 | 1704 | 3016 | 1624 | 17.69953052 | 9.530516432 |
| | 4 | — | — | 301 | — | — |
| | 5 | — | — | 787 | — | — |
| 212C6 | 1 | 1288 | 736 | 564 | 5.714285714 | 4.378881988 |
| | 2 | 1096 | 2276 | 444 | 20.76642336 | 4.051094891 |
| | 3 | 2500 | 45 | 32 | 0.18 | 0.128 |
| | 4 | — | — | 197 | — | — |
| | 5 | — | — | 309 | — | — |
| 212D1 | 1 | 1104 | 2632 | 2461 | 23.84057971 | 22.29166667 |
| | 2 | 460 | 1912 | 600 | 41.56521739 | 13.04347826 |
| | 3 | 1252 | 1788 | 1504 | 14.28115016 | 12.01277955 |
| 256D4 | 1 | 1584 | 1420 | 640 | 8.964646465 | 4.04040404 |
| | 2 | 708 | 156 | 92 | 2.203389831 | 1.299435028 |
| | 3 | 2152 | 162 | 53 | 0.752788104 | 0.246282528 |
| | 4 | — | — | 24 | — | — |
| | 5 | — | — | 35 | — | — |
| 212C6 (undifferentiated clone) | 1 | 4084 | 1868 | 420 | 4.573947111 | 1.028403526 |
| | 2 | 6656 | 576 | 308 | 0.865384615 | 0.462740385 |
| | 3 | 5986 | 1672 | 802 | 2.793184096 | 1.33979285 |
| | 4 | — | — | 433 | — | — |
| | 5 | — | — | 849 | — | — |

While the present invention has been described with emphasis on preferred embodiments, it is obvious to those skilled in the art that the preferred embodiments can be modified. The present invention intends that the present invention can be embodied by methods other than those described in detail in the present specification. Accordingly, the present invention encompasses all modifications encompassed in the gist and scope of the appended "CLAIMS."

In addition, the contents disclosed in any publication cited herein, including patents and patent applications, are hereby incorporated in their entireties by reference, to the extent that they have been disclosed herein.

The invention claimed is:

1. A method of identifying a clonal induced pluripotent stem (iPS) cell line that is not resistant to differentiation comprising the steps of:
   (1) culturing cells of a clonal iPS cell line in retinoic acid such that differentiation occurs;
   (2) culturing the cells obtained in step (1) under conditions for maintaining pluripotent stem cells such that colonies of pluripotent stem cells occur;
   (3) determining the number of colonies of pluripotent stem cells in the cells obtained in step (2); and
   (4) identifying a clonal iPS cell line as being not resistant to differentiation when the number of colonies determined in step (3) is less than or equal to the number of colonies of pluripotent stem cells obtained when an equal number of embryonic stem (ES) cells are cultured under the same conditions as in steps (1) and (2).

2. The method according to claim 1, wherein the retinoic acid concentration is not less than 300 nM and not more than 1000 nM.

3. The method according to claim 1, wherein the duration of retinoic acid treatment is 4 days.

4. The method according to claim 1, wherein the cells are cultured on feeder cells in step (2).

5. The method of claim 1, wherein the retinoic acid concentration is 300 nM.

6. The method of claim 5, wherein the number of colonies determined in step (3) is not more than 250 colonies per 200,000 iPS cells cultured in step (1).

7. The method of claim 5, wherein the number of colonies determined in step (3) is not more than 216 colonies per 200,000 iPS cells cultured in step (1).

8. The method of claim 5, wherein the number of colonies determined in step (3) is not more than 300 colonies per 200,000 iPS cells cultured in step (1).

9. The method according to claim 1, wherein the retinoic acid concentration is 1000 nM.

10. The method of claim 9, wherein the number of colonies determined in step (3) is not more than 20 colonies per 200,000 iPS cells cultured in step (1).

11. The method of claim 9, wherein the number of colonies determined in step (3) is not more than 14 colonies per 200,000 iPS cells cultured in step (1).

12. The method of claim 9, wherein the number of colonies determined in step (3) is not more than 50 colonies per 200,000 iPS cells cultured in step (1).

* * * * *